US006465000B1

(12) United States Patent
Kim

(10) Patent No.: US 6,465,000 B1
(45) Date of Patent: Oct. 15, 2002

(54) METHOD FOR PENILE AUGMENTATION WITH AUTOGENOUS DERMAL CELL CULTURE

(76) Inventor: Jeoung Yong Kim, 607-1105, Mokdong Apt., Mok 6-dong, Yangchun-gu, Seoul 158-056 (KR)

( * ) Notice: Subject to any disclaimer, the term of this patent is extended or adjusted under 35 U.S.C. 154(b) by 37 days.

(21) Appl. No.: 09/660,192

(22) Filed: Sep. 12, 2000

(30) Foreign Application Priority Data

Jun. 9, 2000 (KR) .............................. 00-31695

(51) Int. Cl.[7] .......................... A61F 13/00; A61F 2/00; C12N 5/02
(52) U.S. Cl. ..................... 424/422; 424/426; 435/325; 435/366; 435/371; 604/503
(58) Field of Search ................. 424/422, 426; 604/503; 435/325, 366, 371

(56) References Cited

U.S. PATENT DOCUMENTS

| 5,830,507 A | 11/1998 | Armstrong |
| 5,863,984 A | 1/1999 | Doillon et al. |
| 5,916,265 A | * 6/1999 | Hu .............................. 623/11 |
| 6,054,142 A | 4/2000 | Li et al. |

OTHER PUBLICATIONS

Lindgren et al., Singel and Multiple Dermal Grafts for the Management of Severe Penile Curvature, J. Vrol Sep. 1998, vol. 160 pp. 1128–1130.*

Eardley, Ian, and Krishna Sethia, "Peyronie's Disease", in *Erectile Dysfunction,* Chapter 12, pp. 103–111, 1998.

Ehrlich, Richard M., and Gary J. Alter, "Aesthetic Surgery of the Male Genitalia", in *Reconstructive and Plastic Surgery of the External Genitalia: Adult and Pediatric,* Chapter 79, pp. 463–464, 1999.

Ehrlich, Richard M., and Gary J. Alter, "Treatment of Peyronie's Disease with Plaque Incision of Excision and Dermal Graft", in *Reconstructive and Plastic Surgery of the External Genitalia: Adult and Pediatric,* Chapter 82, pp. 491–494, 1999.

* cited by examiner

*Primary Examiner*—James Ketter
*Assistant Examiner*—Qian J Li
(74) *Attorney, Agent, or Firm*—Finnegan, Henderson, Farabow, Garrett & Dunner LLP

(57) ABSTRACT

The present invention relates to a penile augmentation method comprising culturing autodermal cells in a laboratory and inserting this into penis by using scaffold. This method has advantage of operation convenience, and causes no foreign body sensation after operation and no side effect.

5 Claims, 2 Drawing Sheets

METHOD FOR PENILE AUGMENTATION WITH AUTOGENOUS DERMAL CELL CULTURE

This application claims the benefit of Korean Application 2000-31695, filed Jun. 9, 2000.

FIELD OF THE INVENTION

The present invention relates to a penile augmentation method, specifically to a novel penile augmentation method based on the autogenous dermal cell culture.

BACKGROUND OF THE INVENTION

Since 1920's, various methods for the augmentation of small penis have been attempted in Korea. Examples of such methods include silicon ring operation, fat injection after liposuction, dermo-fat graft augmentation and penile augmentation. As for the method of inserting foreign substance such as silicon ring into the body, however, patients frequently complain of foreign body sensation, and the silicon used has not been internationally verified or domestically approved. Furthermore, fat injection after liposuction has the risk of initial infection, and most of the fat injected is ultimately reabsorbed. Therefore, many urologists prefer dermo-fat graft augmentation. However, it has the following disadvantages: about 10–20 cm length of skin incision in the buttocks or lower abdominal region; inability to perform the augmentation operation under local anesthesia; initial infection; irregular and uneven shape due to fat re-absorption; and a contraction causing penile induration.

SUMMARY OF THE INVENTION

As a result of intensive studies, the present inventor developed a novel penile augmentation method based on autogenous dermal cell culture, which produces little foreign body sensation and whose operation procedure is simple and convenient.

The present invention relates to a penile augmentation method comprising: culturing human dermis cells to obtain cultured dermis cells; inserting scaffold into penis; and loading said cultured dermis cells into said scaffold.

DETAILED DESCRIPTION OF THE INVENTION

1. Culture of Human Dermal Cells

In order to prepare dermal cells to be cultured and loaded into penis, parts of dermal cells are extracted from human body. Penile skin is preferable as the extraction site. After incising an adequate amount of dermal cells (e.g., 1×2 cm) from body, only a dermal layer is separated to obtain a dermal tissue. Then, it is soaked with Clostridium type colagenease IV (Gibco, NY, USA) or serum-free cell culture media (e.g., FGM® Bullet Kit (Biowhitaker, MD, USA)), and minced by cutting into 1 mm pieces.

The minced tissue is put into a culture flask, and an adequate amount of a mixture containing aminomax® (Gibco, NY, USA) (80~90%) and autologous human serum (10~20%), or cell culture media containing 10% human synthetic serum substrate (Irvine Scientific, CA) is added thereto, and culture is performed in an incubator.

The culture media used is a commercialized one, for which sterilization, virus test and toxicity test were carried out. After 2 weeks of the culture, the bottom of the flask is completely covered with cells. The cells are then harvested by treating with 0.1% trypsin. It is preferable to adjust the number of the harvested cells to $(5–10) \times 10^8$. When using the cultured cells, they are again dispersed in 1–2 ml of culture media, for use in 30 minutes.

2. Biodegradable Polymer

In order to load the cultured dermal cells into penis, the use of scaffold is required. As the material for such scaffold, substance that can be degraded in a living body and also safe to body may be used. Preferably, Terudermis® (Terumo, Japan), commercially available bio-substance for tissue reconstruction, can be used. When such scaffold is inserted into skin and the cultured tissue cells are loaded therein, scaffold itself then disappears in 2–4 weeks by degradation, and a new dermal layer is formed within the body by the loaded cells.

3. Insertion of Scaffold and Cell-loading

As explained above, dermal tissue is obtained from human body, and dermis cells are cultured in laboratory to prepare cultured cells. Then a scaffold, biodegradable polymer, is inserted into the penis of the patient who will undergo a penile augmentation. The region where scaffold is inserted is about 4–6 cm of the ventral region that is located in 1 cm below penis glans. The amount of scaffold inserted is variable depending on the patient.

After the insertion of the scaffold, a suspension is prepared by suspending the cultured cells into a cell culture media, and the resulting suspension is injected to the scaffold. After the injection, suitable treatment is performed so that scaffold is not overly tightened, and skin is closed carefully. Stiches-out is possible about 1 week after the operation, and intercourse is generally possible 3–4 weeks after the surgery.

Figure 1:
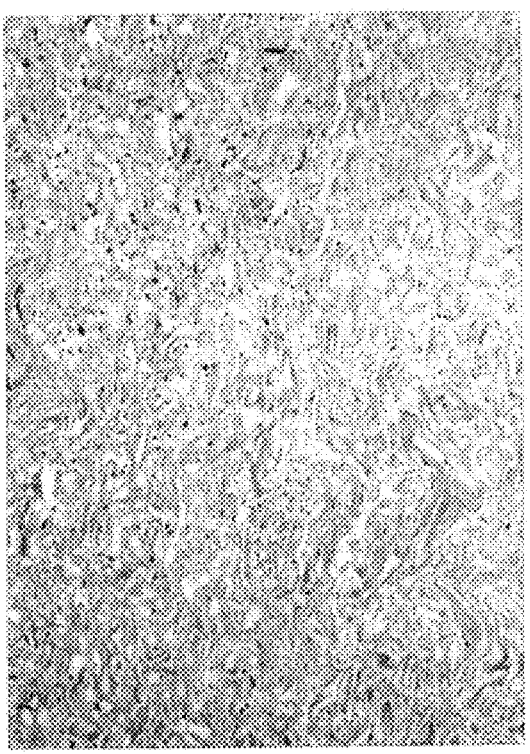
FIG. 1 is a photograph and its enlargement photograph showing the cross-section of the tissue 6 months after the insertion of cultured dermal cells into penis according to the present invention.
Figure 1:
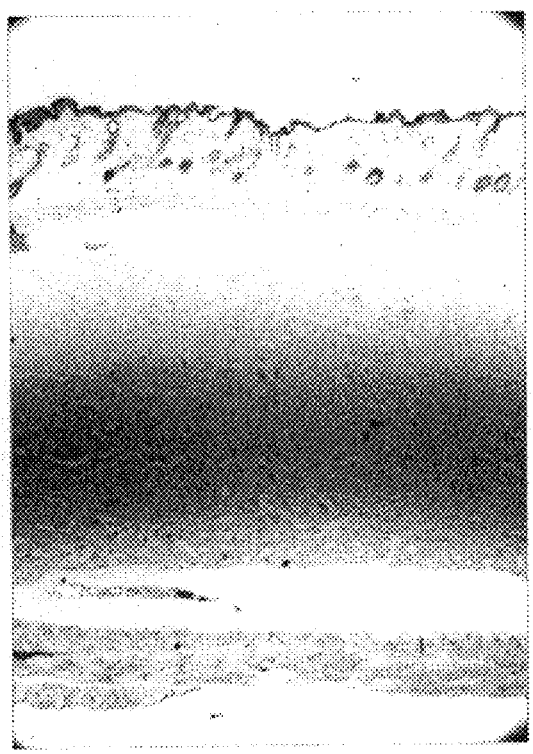

FIG. 1 is a photograph and its enlargement photograph showing the cross-section of the tissue 6 months after the insertion of cultured dermal cells into penis according to the present invention. It can be seen in FIG. 1 that a new dermal layer was formed.

In order that this invention may be better understood, the following examples are set forth. These examples are for purposes of illustration only and are not to be construed as limiting the scope of this invention in any manner.

EXAMPLE 1

Culture of Human Dermis Cell

1. Subject

Among the patients who are more than 20 years old, and whose penis is shorter than 6 cm upon measuring a stretched penis from penopubic junction to the tip of glans, or less than 7 cm in its circumference, 42 persons who have strong desire for the penile augmentation were selected. The selected patients consist of 2 persons in sixties, 10 persons in fifties, 21 persons in forties, 7 persons in thirties and 2 persons in twenties.

2. Cell Culture

After local anesthesia, scrotal skin was incised through about 1 cm length, and a dermal tissue of 1×2 cm in area was obtained by the separation of dermis layer. The dermal tissue was soaked with serum-free culture media FGM® Bullet Kit (Biowhitaker, MD, USA), and minced by cutting into 1 mm pieces. This was put into four tissue-culture flasks of 25 mm² in volume (Nunc, USA), and about 5 ml of a mixture containing Aminomax® (Gibco, NY, USA) (80~90%) and autologous human serum (10~20%) was added thereto and incubated in 5% $CO_2$ incubator at 37° C. As for the media, a commercialized media was used, for which sterilization treatment, virus test and toxicity test were already performed. As the reagent, a finished product, or product that has undergone a sterilization with 0.2 μm porous filter was used. Before using the cell culture media, its side effects were tested by injecting 1 cc of the culture media into 10 adult male via subcutaneous route.

Figure 2:
FIG. 2 is a photograph showing the skin of Nude Mouse, in which dermal layer was formed according to the present invention.

Cell culture media was filled-up 2 days after the initiation of the culture, and if cell colony is found upon observation with optical microscope after 6 days, floating dead cells were removed and washed once with cell culture media, and then about 5 ml of culture media per each flask was replaced every 2 days. When a layer is formed owing to the excess multiplication of cells, cells were separated from the bottom of flask by using cell spreader, or by tapping the flask with hand after incubation for 2 minutes at 37° C. after treatment with 0.1% trypsin, and again 5 ml of culture media was added. When the bottom of the flask was wholly covered with cells after 2 weeks of the incubation (FIG. 2), cells were harvested by 0.1% trypsin treatment, the number of cells was adjusted to be in range of $5-10\times10^3$, and the cells were subjected to floating in 1–2 ml of cell culture media, for use within 30 minutes.

EXAMPLE 2

Animal Test

As scaffold, 1×1 cm Terudermis (Terumo, Japan) was inserted into flank subcutaneous layer of 10 Nude Mice (two weeks' old), and to 5 mice among them, $5\times10^8$/ml of human dermis cells, which were cultured in Example 1, were uniformly loaded into the scaffold by injection. One month after the cell loading, 10 Nude Mice were all killed, skin tissue of the cell-loading area was taken, main organs were extracted, and H&E staining was performed to observe with optical microscope.

As a result, in case of the group where cultured dermis cells were injected after the insertion of Terudermis, new dermis layer with 3 mm thickness in average, was formed (FIG. 2), while in case of the group where only Terudermis was inserted without injecting the cultured cells, new dermis layer of 1 mm thickness was formed. Tissue impression on the extracted main organs (liver, spleen, kidney, testis and brain) was normal.

EXAMPLE 3

Clinical Test

The subjects tested were all 42 persons. About 5 cm circumferential incision was performed at each subject's ventral region 1 cm below the penis glans, then the whole part of penis ventral region under dartos fascia was opened, and 4×7 cm of 3 or 4-layered Terudermis was inserted. Skin was closed and cell culture suspension prepared in Example 1 was uniformly injected into the inserted Terudermis via 3 cc syringe. After the injection, penis was loosely dressed, and stitches-out was carried out at 7 days after the operation.

As a result, incidence of complication in 1–2 weeks after the operation was low, that is, pressure necrosis of upper skin occurs in case of excessive (4-layered) insertion of Terudermis (1 patient), stitches abscess (2 patients), and skin vesicles (1 patient). For the patient showing pressure necrosis, Terudermis was removed.

One month after the operation, postoperative follow-up was performed to 16 patients. As a result, 1 patient showed a penile girth increase of 1 cm or less, 2 patients showed 1–1.5 cm increase, 9 patients showed 2.0–2.5 cm increase, and 4 patients showed increase more than 2.5 cm. In other words, most patients showed penile girth increase of at least 1.5 cm (Table 1). Furthermore, the penis did not exhibit contraction, and its palpation was soft, and patients were all pleased with the result.

TABLE 1

| Penile Girth Increase | Number of Patients |
| --- | --- |
| Less than 1 cm | 1 |
| 1–1.5 cm | 2 |
| 2.0–2.5 cm | 9 |
| More than 2.5 cm | 4 |
| Total | 16 |

What is claimed is:

1. A penile augmentation method comprising: culturing autologous human dermis cells to obtain an expanded population of cultured dermis cells; inserting a biodegradable scaffold into a penis; and loading said cultured dermis cells into said inserted scaffold.

2. The method in claim 1, wherein said culturing step comprises: separating part of dermis cells from body; mincing said separated dermis cells; and putting said minced dermis cells into cell culture media to perform culturing.

3. The method in claim 2, wherein said culture is carried out in 5% $CO_2$ incubator at 37° C.

4. The method in claim 1, wherein said scaffold is atelocollagen.

5. The method in claim 1, wherein said scaffold is inserted into 4–6 cm of ventral region that is located 1 cm below the penis glans.

* * * * *